US009787274B2

(12) United States Patent
Butts

(10) Patent No.: US 9,787,274 B2
(45) Date of Patent: Oct. 10, 2017

(54) AUTOMATIC SOUND EQUALIZATION DEVICE

(71) Applicant: Harman International Industries, Inc., Stamford, CT (US)

(72) Inventor: Donald Joseph Butts, Westport, CT (US)

(73) Assignee: HARMAN INTERNATIONAL INDUSTRIES, INCORPORATED, Stamford, CT (US)

( * ) Notice: Subject to any disclaimer, the term of this patent is extended or adjusted under 35 U.S.C. 154(b) by 69 days.

(21) Appl. No.: 14/918,239

(22) Filed: Oct. 20, 2015

(65) Prior Publication Data
US 2016/0112022 A1 Apr. 21, 2016

Related U.S. Application Data

(60) Provisional application No. 62/066,274, filed on Oct. 20, 2014.

(51) Int. Cl.
*H03G 5/00* (2006.01)
*H03G 5/16* (2006.01)
(Continued)

(52) U.S. Cl.
CPC ............ *H03G 5/165* (2013.01); *A61B 5/125* (2013.01); *A61N 1/36032* (2013.01); *G06F 3/015* (2013.01); *H04R 1/10* (2013.01); *H04R 5/04* (2013.01); *A61B 5/04845* (2013.01); *H04R 3/04* (2013.01); *H04R 25/70* (2013.01)

(58) Field of Classification Search
CPC ............ H04R 25/70; H04R 3/04; H04R 1/10; H04R 5/04; H03G 5/165; G06F 3/015; A61B 5/04845; A61B 5/125; A61N 1/36032
See application file for complete search history.

(56) References Cited

U.S. PATENT DOCUMENTS

2005/0094822 A1 5/2005 Swartz
2007/0195963 A1 8/2007 Ko et al.
(Continued)

FOREIGN PATENT DOCUMENTS

WO 9836711 A1 8/1998
WO 2012056427 A1 5/2012

OTHER PUBLICATIONS

European Search Report Application No. 15190577.5, dated Apr. 26, 2016, 7 pages.

*Primary Examiner* — Regina N Holder
(74) *Attorney, Agent, or Firm* — Artegis Law Group, LLP

(57) ABSTRACT

A technique for determining one or more equalization parameters includes acquiring, via one or more electrodes, auditory brainstem response (ABR) data associated with a first audio sample and determining, via a processor, one or more equalization parameters based on the ABR data. The technique further includes reproducing a second audio sample based on the one or more equalization parameters, acquiring, via the one or more electrodes, complex auditory brainstem response (cABR) data associated with the second audio sample, and comparing, via the processor, the cABR data to at least one representation of the second audio sample to determine at least one measure of similarity. The technique further includes modifying the one or more equalization parameters based on the at least one measure of similarity.

20 Claims, 6 Drawing Sheets

(51) Int. Cl.
*G06F 3/01* (2006.01)
*A61N 1/36* (2006.01)
*H04R 5/04* (2006.01)
*A61B 5/12* (2006.01)
*H04R 1/10* (2006.01)
H04R 3/04 (2006.01)
H04R 25/00 (2006.01)
A61B 5/0484 (2006.01)

(56) References Cited

U.S. PATENT DOCUMENTS

2011/0150253 A1 6/2011 Corona-Strauss et al.
2012/0197153 A1 8/2012 Kraus et al.

AUTOMATIC SOUND EQUALIZATION DEVICE

CROSS-REFERENCE TO RELATED APPLICATIONS

This application claims benefit of the United States provisional patent application having Ser. No. 62/066,274, filed Oct. 20, 2014. The subject matter of this related application is hereby incorporated herein by reference.

BACKGROUND

Field of the Embodiments

The various embodiments relate generally to audio signal processing and, more specifically, to sound equalization devices.

Description of the Related Art

One problem with many audio devices is the reliance on user input for adjusting the characteristics of the sound outputted by the audio device. In particular, a conventional audio device typically relies on a user to manually adjust multiple sound equalization parameters in order to configure the output of the audio device to suit the hearing characteristics of the user. For example, many mobile devices provide users with an option to adjust the relative gains of several different frequency bands (e.g., low frequency bands, mid-range frequency bands, and high frequency bands).

However, while many audio devices provide users with options to fine tune sound output via multiple settings, many users are unable to properly utilize such settings to configure the outputs of their audio devices to match their hearing characteristics or personal preferences. For example, properly adjusting equalization parameters can require multiple iterations of adjusting the equalization parameters associated with multiple different frequency bands, given that the equalization parameter associated with any one frequency band may affect the perception of sound associated with the other frequency bands. Consequently, a user may spend a significant amount of time adjusting different equalization parameters without actual finding a combination of settings that properly match his/her specific hearing characteristics.

Further, although various types of audiology devices are available for determining user hearing thresholds as a function of audio frequency, determining hearing thresholds via such devices is cumbersome. For example, conventional techniques for determining user hearing thresholds require the user to listen to a series of tones having different volumes and frequencies and then indicate which of the tones is audible. Such tests are not only time-consuming, the tests may not accurately reflect the manner in which the user would respond to more complex audio samples, such as a music track. Consequently, users tend not to use such devices to help determine their hearing thresholds.

As the foregoing illustrates, more effective techniques for determining sound equalization parameters associated with audio devices that are tailored to the preferences of end-users would be useful.

SUMMARY

Embodiments of the present disclosure set forth a method for determining one or more equalization parameters. The method includes acquiring, via one or more electrodes, auditory brainstem response (ABR) data associated with a first audio sample and determining, via a processor, one or more equalization parameters based on the ABR data. The method further includes reproducing a second audio sample based on the one or more equalization parameters, acquiring, via the one or more electrodes, complex auditory brainstem response (cABR) data associated with the second audio sample, and comparing, via the processor, the cABR data to at least one representation of the second audio sample to determine at least one measure of similarity. The method further includes modifying the one or more equalization parameters based on the at least one measure of similarity.

Further embodiments provide, among other things, a system and a non-transitory computer-readable storage medium configured to implement the techniques set forth above.

At least one advantage of the disclosed technique is that signals indicative of user brain activity can be analyzed to more accurately determine sound parameters for multiple frequency bands. Additionally, sound parameters can be determined while a user is listening to various types of complex audio samples, such as a music track, without requiring the user to listen to a lengthy series of tones. Accordingly, the user does not need to spend a significant amount of time and effort calibrating the audio device.

BRIEF DESCRIPTION OF THE SEVERAL VIEWS OF THE DRAWINGS

So that the manner in which the recited features of the one or more embodiments set forth above can be understood in detail, a more particular description of the one or more embodiments, briefly summarized above, may be had by reference to certain specific embodiments, some of which are illustrated in the appended drawings. It is to be noted, however, that the appended drawings illustrate only typical embodiments and are therefore not to be considered limiting of its scope in any manner, for the scope of the various embodiments subsumes other embodiments as well.

DETAILED DESCRIPTION

In the following description, numerous specific details are set forth to provide a more thorough understanding of the embodiments of the present disclosure. However, it will be apparent to one of skill in the art that the embodiments of the present disclosure may be practiced without one or more of these specific details.

Figure 1:
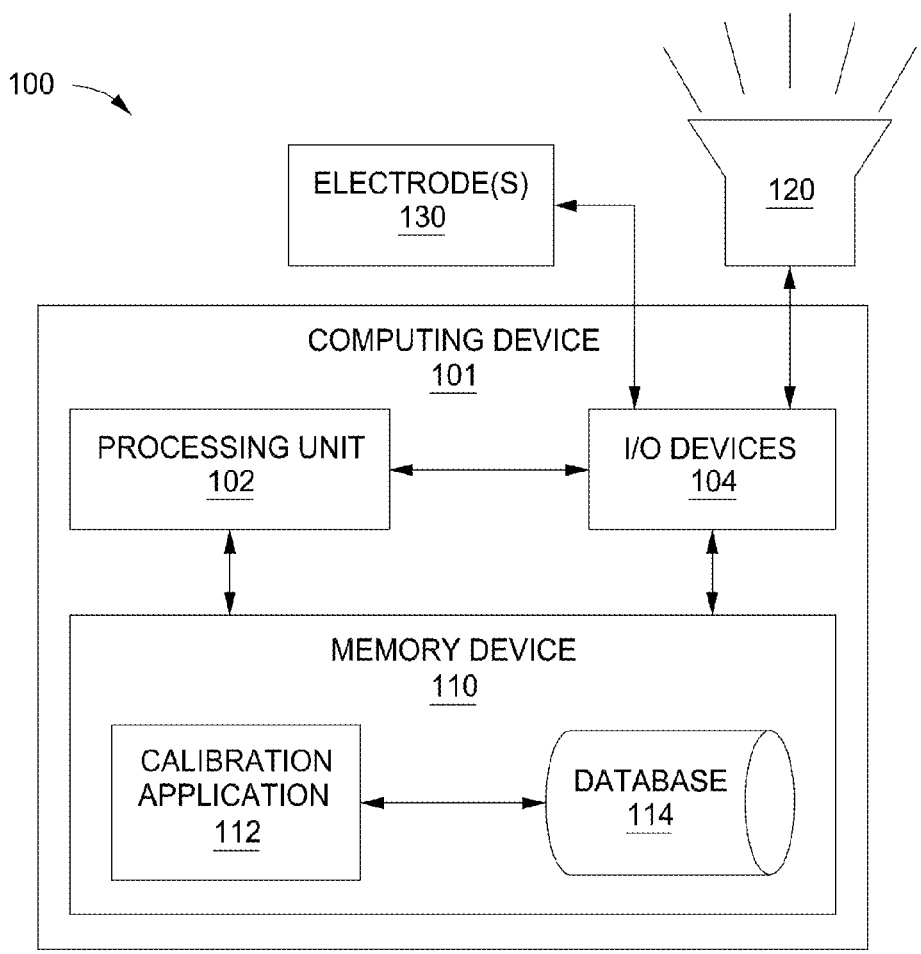
FIG. 1 illustrates an audio device for determining sound parameters associated with the hearing characteristics of a user, according to various embodiments.

FIG. 1 illustrates an audio device 100 for determining sound parameters associated with the hearing characteristics of a user, according to various embodiments. The audio device 100 may include, without limitation, a computing device 101, one or more speakers 120, and one or more electrodes 130. The computing device 101 includes a processing unit 102, input/output (I/O) devices 104, and a memory device 110. The memory device 110 includes a calibration application 112 configured to interact with a database 114.

In some embodiments, audio device 100 may include a personal audio device, mobile computer, personal digital assistant, mobile phone, desktop computer, diagnostic device, medical device, or any other device suitable for practicing one or more embodiments. In general, the audio device 100 determines how the brain of a user responds to various sound frequencies by playing one or more audio samples via the speaker(s) 120 while acquiring signals indicative of brain activity via the electrode(s) 130. The calibration application 112 then compares the signals to an analysis of the audio sample(s), adjusts various audio parameters based on the comparison, and repeats the process by playing an additional audio sample based on the updated audio parameters and acquiring signals via the electrode(s) 130, if necessary.

The electrode(s) 130 may include one or more electroencephalography (EEG) electrodes implemented in a sensor array. In various embodiments, the sensor array includes at least three electrodes. The electrodes 130 are configured to measure a vector of the average electrical activity produced in the brain of a user. In some embodiments, the electrodes 130 capture EEG auditory brainstem response (ABR) signals and/or complex auditory brainstem response (cABR) signals and provide the signals to the computing device 101. For example, and without limitation, the electrodes 130 could be configured to measure microvolt (μV) electrical signals produced in the brain of a user in response to various stimuli, such as when an audio sample (e.g., a click or chirp excitation, a voice sample, or a music track) is played for the user via the speaker(s) 120. In general, the audio device 100 may include any number of electrodes 130 configured to be placed in contact with a user's scalp, ear canal, and/or other portions of the user's head or body.

Processing unit 102 may include a central processing unit (CPU), digital signal processing unit (DSP), and so forth. Memory device 110 includes a memory module or a collection of memory modules. The calibration application 112 within memory device 110 is executed by processing unit 102 to implement the overall functionality of the computing device 101 and, thus, to coordinate the operation of the audio device 100 as a whole. For example, and without limitation, audio samples and/or signals acquired via the electrodes 130 may be processed by the calibration application 112 using time, frequency, or time-frequency domain analysis (e.g. spectrogram, wavelets) to generate audiograms, hearing loss thresholds, and/or audio parameters (e.g., equalization parameters, compression parameters, etc.). In some embodiments, calibration application 112 further performs statistical analysis on audio samples and/or signals acquired via the electrodes 130. In some embodiments, the database 114 stores audio samples, audio parameters, ABR data, cABR data, algorithms, statistics, and user preferences.

I/O devices 104 may include input devices, output devices, and devices capable of both receiving input and providing output. For example, and without limitation, I/O devices 104 may include wired and/or wireless communication devices that send data to and/or receive data from the speaker(s) 120 and/or electrodes(s) 130 included in the audio device 100. Additionally, the I/O devices 104 may include one or more wired or wireless communication devices that receive signals (e.g., ABR and/or cABR signals) indicative of user brain activity.

In various embodiments, computing device 101 includes a microprocessor, an application-specific integrated circuit (ASIC), a system-on-a-chip (SoC), etc., that is included in a personal audio device, headphones, in-ear audio devices, a mobile computing device such as a wearable mobile device, a tablet computer or cell phone, a media player, diagnostic device, medical device, and so forth. Generally, computing device 101 is configured to coordinate the overall operation of the audio device 100. In other embodiments, the computing device 101 may be coupled to, but separate from other components of the audio device 100. In such embodiments, the audio device 100 may include a separate processor that receives signals indicative of brain activity from the electrode(s) 130 and transmits data (e.g., ABR data and/or cABR data) to the computing device 101, which may be included in a separate device, such as a personal computer, wearable device, smartphone, portable media player, etc. However, the embodiments disclosed herein contemplate any technically feasible system configured to implement the functionality of the audio device 100.

Figure 2:
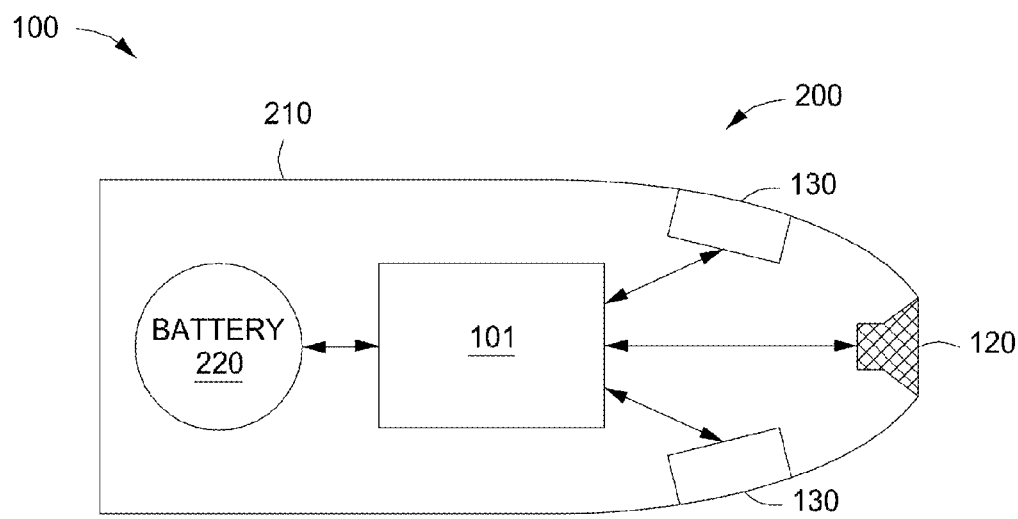
FIG. 2 illustrates an earphone that implements the audio device of FIG. 1, according to various embodiments.

FIG. 2 illustrates an earphone 200 with which the audio device 100 of FIG. 1 may be implemented for determining sound parameters, according to various embodiments. As shown, the earphone 200 includes, without limitation, an earphone body 210, computing device 101, a speaker 120, one or more electrodes 130, and a battery 220. The earphone body 210 may include a flexible material, such as a polymer, foam, silicone, rubber, etc., that conforms to the ear canal of the user and provides some degree of isolation from noises in the surrounding environment.

The earphone body 210 may be shaped to fit the ear canal of a variety of different users, or the earphone body 210 may be shaped to fit the ear canal of a specific user, such as by custom molding the earphone body 210 to the ear canal of a user. In other embodiments, the earphone body 210 includes a non-flexible material, such as hard plastic or metal, and/or may not provide substantial isolation from noise in the surrounding environment.

In one embodiment, the electrode(s) 130 are integrated into the earphone 200 and in contact with the ear canal of the user. In other embodiments, the electrodes 130 may be separate from the earphone body 210 and may be in contact with the scalp of the user and/or to other portions of the head and/or body of the user. In such embodiments, the electrodes 130 are in communication with the computing device 101 via one or more traces and/or via a wireless protocol.

The speaker 120 is located in a portion of the earphone body 210 that faces inward, towards the ear canal of the user. The speaker 120 is configured to produce sounds based on audio signals that are generated by the computing device 101 and/or other signals that are transmitted to the speaker 120. For example, and without limitation, the speaker 120 could be configured to produce audio samples generated by the calibration application 112. Such audio samples may be reproduced for the user based on hearing thresholds and/or sound parameters determined by the calibration application 112. Processing performed by the computing device 101 may include, without limitation, filtering, amplification, attenuation, and/or other types of auditory enhancements. In some embodiments, audio parameters (e.g., hearing thresholds, equalization parameters, compression parameters, etc.) are stored in the memory 110 of the computing device 101.

In some embodiments, the speaker 120 is configured for high-fidelity sound reproduction. In other embodiments, in order to reduce the size and/or cost of the speaker 120, the speaker 120 may be configured for less accurate sound reproduction. For example, and without limitation, in some embodiments, the speaker 120 is configured to produce only a subset of frequencies within the normal human hearing range.

Although the audio device 100 shown in FIG. 2 is implemented with an earphone 200, in other embodiments, the audio device 100 may be included in and/or coupled to other types of devices. For example, and without limitation, the audio device 100 could be included in a pair of over-the-ear headphones, circumaural headphones, or earbuds. Additionally, multiple audio devices 100 may be operated in conjunction with one another to reproduce audio samples for a user, acquire signals indicative of user brain activity, and/or analyze such signals to determine sound parameters. For example, and without limitation, an audio device 100 integrated with a head-mounted device (e.g., a pair of headphones) could reproduce audio samples and acquire signals indicative of user brain activity while an audio device 100 integrated with a consumer electronics device, such as a smartphone, personal computer, etc. may process the audio samples and/or signals to determine sound parameters.

Figure 3:
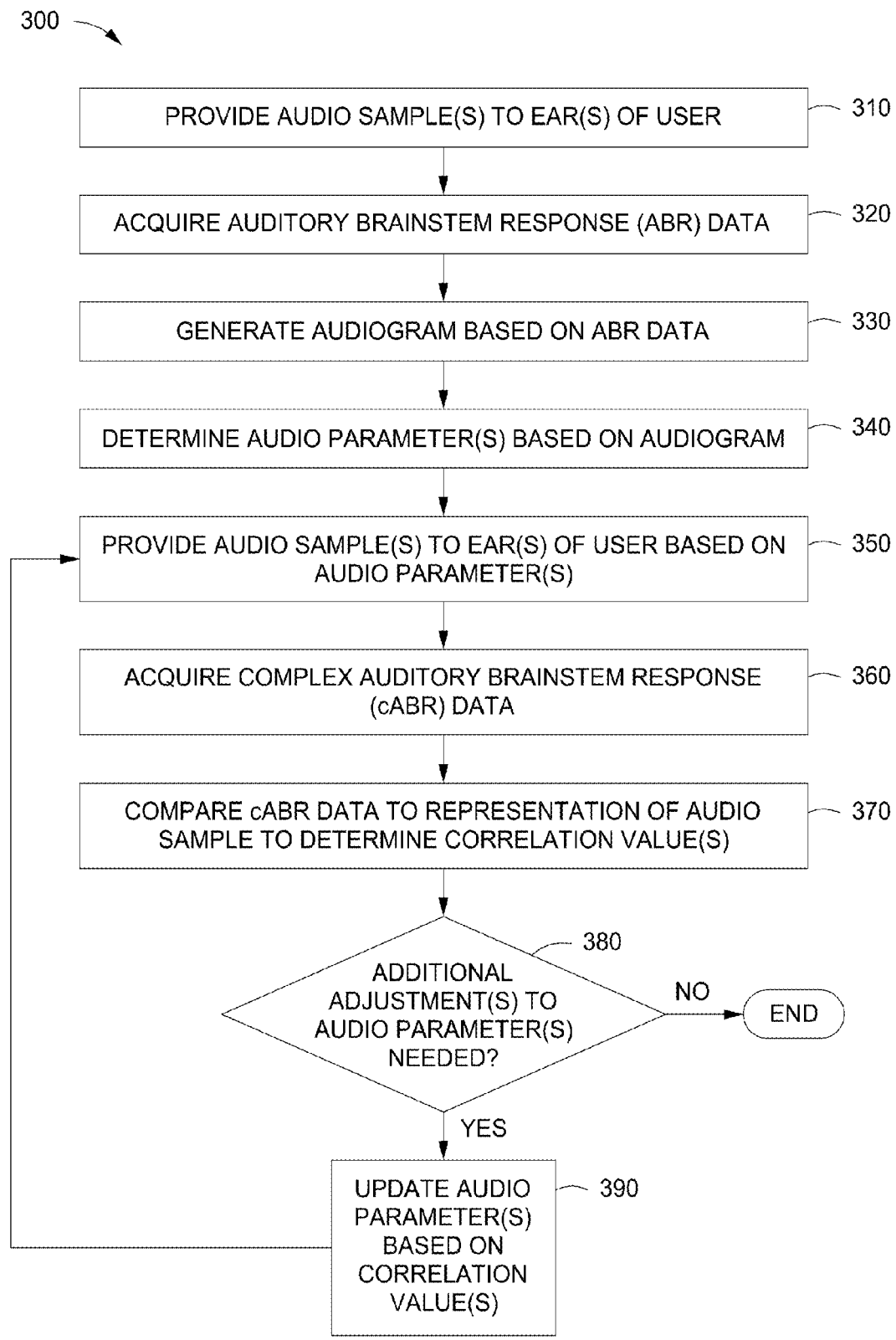
FIG. 3 is a flow diagram of method steps for determining sound parameters associated with the hearing characteristics of a user, according to various embodiments.
Figure 4:
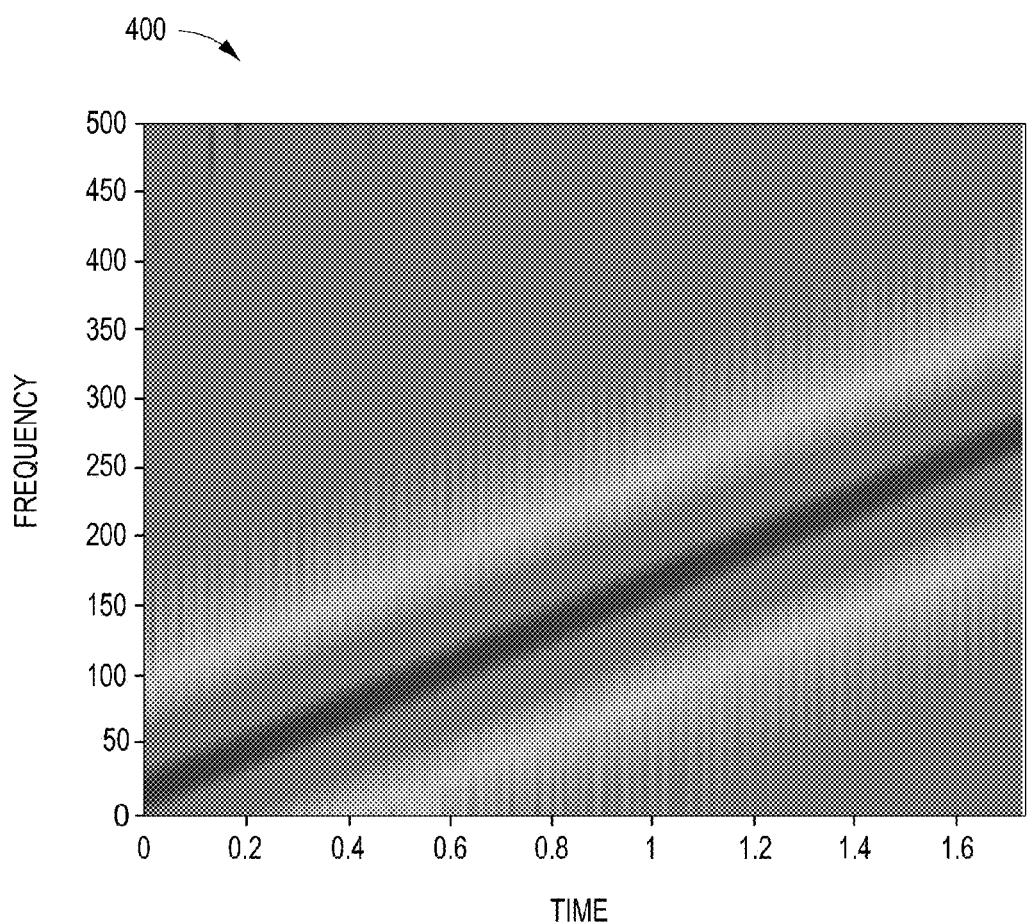
FIG. 4 illustrates the frequency content of an audio sample as a function of time, according to various embodiments.
Figure 5:
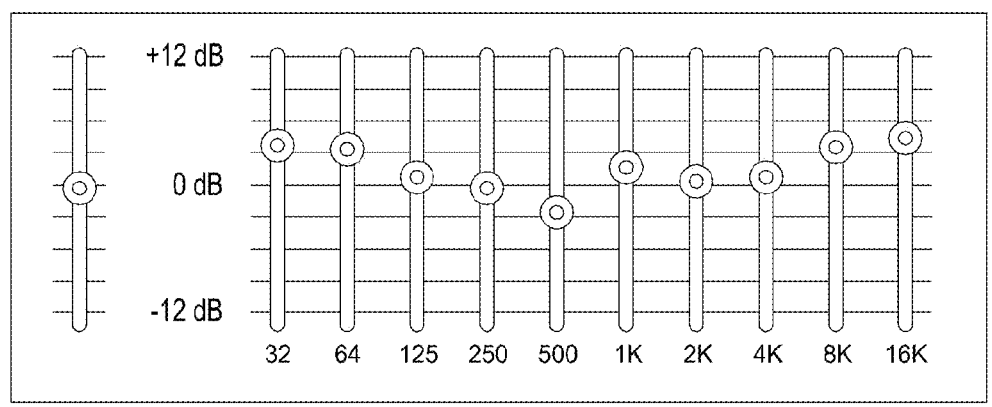
FIG. 5 illustrates an equalizer having equalization parameters associated with ten frequency bands, according to various embodiments.

FIG. 3 is a flow diagram of method steps for determining sound parameters associated with the hearing characteristics of a user, according to various embodiments. Although the method steps are described in conjunction with the systems of FIGS. 1-2, and 4-8, persons skilled in the art will understand that any system configured to perform the method steps, in any order, falls within the scope of the various embodiments.

As shown, a method 300 begins at step 310, where the calibration application 112 provides an audio sample to the ear(s) of the user via the speaker(s) 120. In some embodiments, the audio sample provided via the speaker(s) 120 includes a tone and/or a chirp having a specific frequency or range of frequencies. For example, and without limitation, the audio sample may include the chirp 400 shown in FIG. 4, which illustrates the frequency content of an audio sample as a function of time, according to various embodiments. At step 320, the calibration application 112 acquires ABR data via the electrode(s) 130 while the audio sample is being provided via the speaker(s) 120.

At step 330, the calibration application 112 generates an audiogram based on the ABR data. In some embodiments, the audiogram indicates the hearing thresholds (e.g., in decibels) of a user for multiple audio frequencies and/or audio frequency ranges. At step 340, the calibration application 112 determines one or more audio parameters based on the audiogram. In some embodiments, the audio parameters include equalization parameters and/or compression parameters that specify the relative amplitudes for multiple audio frequencies and/or audio frequency bands. For example, and without limitation, the audio parameters could include the equalization parameters shown in FIG. 5, which illustrates an equalizer having equalization parameters associated with ten frequency bands, according to various embodiments.

At step 350, the calibration application 112 provides one or more additional audio samples to the ear(s) of the user via the speaker(s) 120 based on the audio parameters determined at step 340. In some embodiments, the audio sample(s) provided at step 350 include voice samples, music samples, and/or other types of complex audio samples. In other embodiments, the audio sample(s) provided at step 350 include tones and/or chirps having a specific frequency or range of frequencies.

Figure 6:
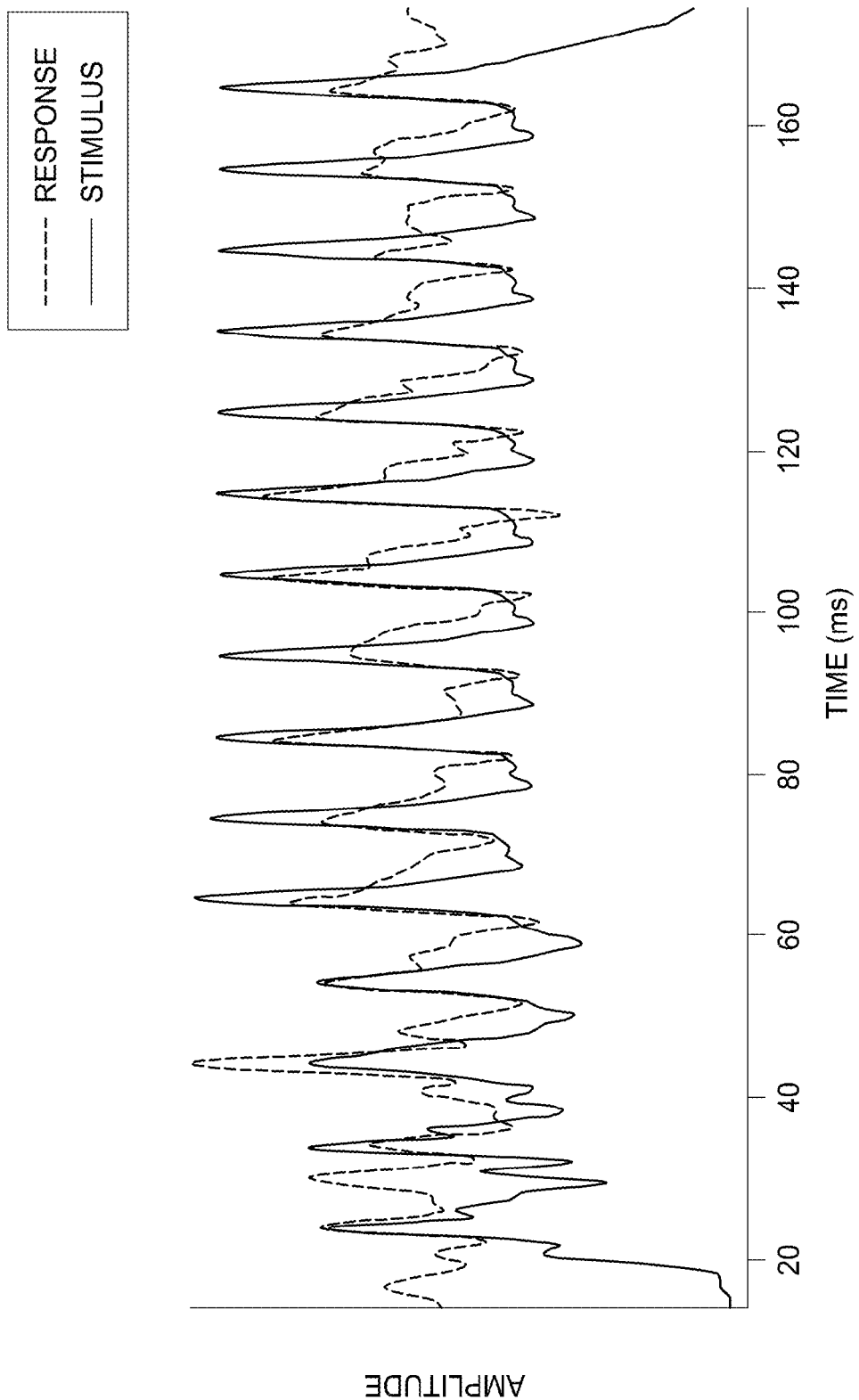
FIG. 6 illustrates the amplitude of brain activity measured via electrodes and the amplitude of an audio sample provided via speakers, according to various embodiments.
Figure 7:
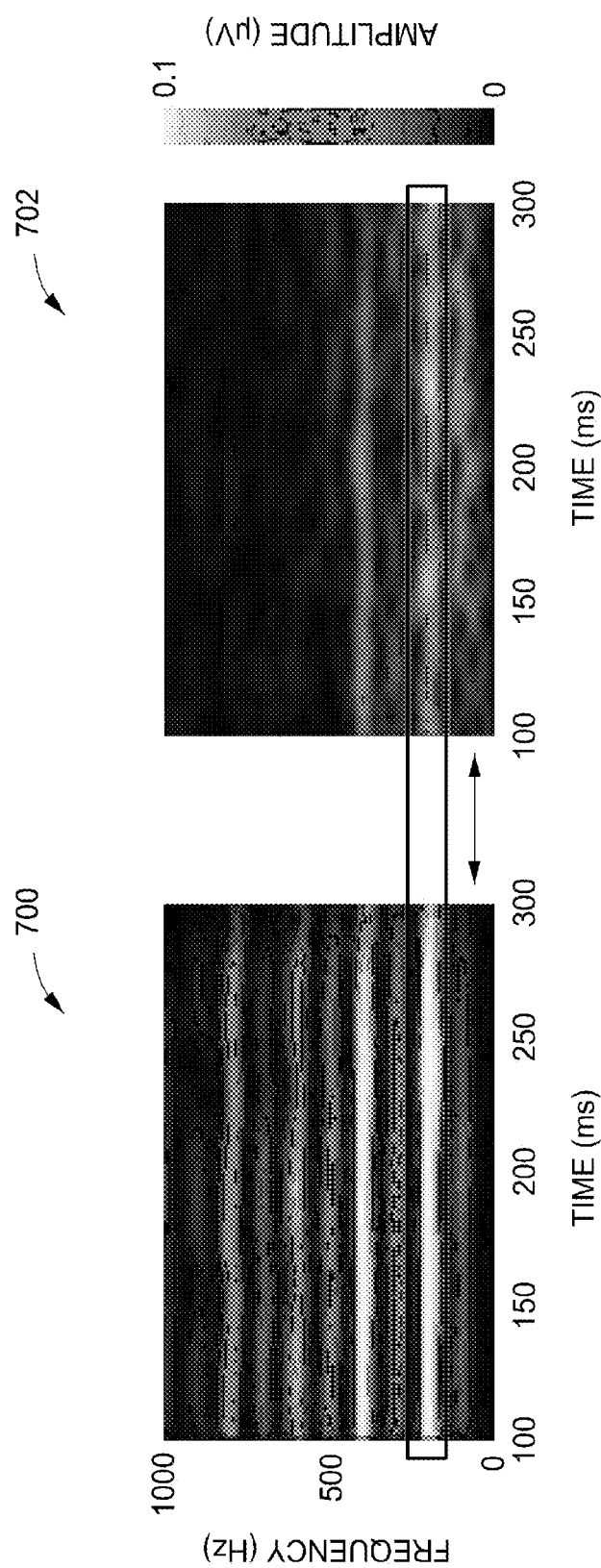
FIG. 7A illustrates the amplitudes of various frequencies included in an audio sample as a function of time, according to various embodiments.
FIG. 7B illustrates the amplitudes of brain activity produced in response to various frequencies included in an audio sample as a function of time, according to various embodiments.

Next, at step 360, the calibration application 112 acquires cABR data via the electrode(s) 130 while the additional audio sample is being provided via the speaker(s) 120. An example of cABR data acquired while an audio sample is being provided to the user is shown in FIG. 6, which illustrates the amplitude of brain activity measured via the electrode(s) 130 and the amplitude of the audio sample provided via the speaker(s) 120, according to various embodiments. In some embodiments, at step 360, the calibration application 112 provides an audio sample to the user multiple times and averages the cABR data acquired via the electrode(s) 130.

At step 370, the calibration application 112 compares the cABR data to a representation of the audio sample to determine one or more measures of similarity. In various embodiments, the measure(s) of similarity determined by the calibration application 112 include correlation values and/or coherence values between the cABR data and the representation of the audio sample, such as a value from 0 to 1. The representation of the audio sample may include a spectrogram and/or wavelet representation of the audio sample. For example, and without limitation, the calibration application 112 could process the audio sample to generate a first spectrogram 700, as shown in FIG. 7A, which illustrates the amplitudes of various frequencies included in the audio sample as a function of time, according to various embodiments. Additionally, and without limitation, the calibration application 112 could process the cABR to generate a second spectrogram 702, as shown in FIG. 7B, which illustrates the amplitudes of brain activity produced in response to various frequencies included in the audio sample as a function of time, according to various embodiments.

Once the first spectrogram 700 and second spectrogram 702 are generated, the spectrograms 700, 702 could be compared to one another via a cross-correlation process to determine one or more measures of similarity. In some embodiments, portions of each of the spectrograms 700, 702 associated with the same filtered frequency range are compared to determine how accurately the user perceived the audio sample. For example, and without limitation, spectrographic data included in the first spectrogram 700 and associated with a first frequency band 710 could be compared to spectrographic data included in the second spectrogram 702 and associated with the first frequency band 710. The calibration application 112 could then determine a measure of similarity based on the degree of similarity between the portions of spectrographic data, where a high degree of similarity indicates that the user more accurately perceived the audio sample, and a low degree of similarity indicates that the user did not accurately perceive the audio sample. The process of comparing spectrographic data included in the first spectrogram 700 to spectrographic data included in the second spectrogram 702 could then be repeated for one or more additional frequency bands in order to determine measures of similarity for the additional frequency bands.

Figure 8:
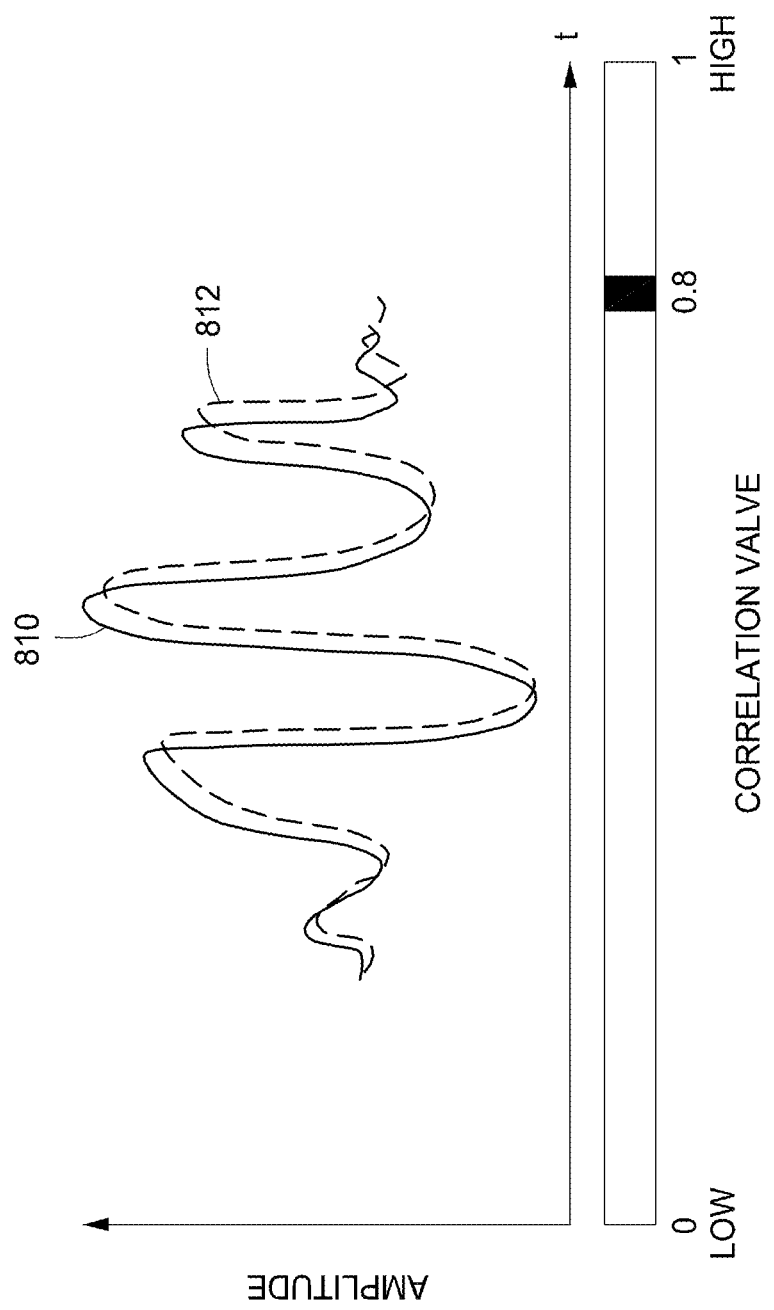
FIG. 8 illustrates a comparison of wavelets generated based on spectrographic data associated with an audio sample and complex auditory brainstem response (cABR) data, according to various embodiments.

In the same or other embodiments, once the first spectrogram 700 and second spectrogram 702 are generated, the spectrograms 700, 702 could be processed to generate one or more wavelets, where each wavelet can be filtered to be associated with a specific frequency or frequency band. For example, and without limitation, a cross-section of the spectrograms 700, 702 could be taken for each of a plurality of different frequency bands to generate wavelets associated with those frequency bands. Each wavelet associated with the audio sample and a given frequency band could then be compared to a corresponding wavelet associated with the cABR data and the same frequency band to determine one or more measures of similarity. For example, and without limitation, a wavelet 810 generated based on the spectrographic data included in the first spectrogram 700 and associated with a frequency band could be compared to a wavelet 812 generated based on the spectrographic data included in the second spectrogram 702 and associated with the same frequency band, as shown in FIG. 8. The calibration application 112 could then determine a measure of similarity based on the degree of similarity between the wavelets 810, 812. The process of comparing a wavelet associated with the audio sample and to a wavelet associated with the cABR data could then be repeated for one or more additional frequency bands in order to determine measures of similarity for the additional frequency bands.

At step 380, the calibration application 112 determines whether the audio parameters should be adjusted based on the measure(s) of similarity. In some embodiments, the calibration application 112 determines whether audio parameters associated with each of a plurality of frequency bands should be adjusted based on the measure(s) of similarity associated with each frequency band. For example, and without limitation, the calibration application 112 may determine whether the measure(s) of similarity determined at step 370 for the first frequency band 710 are above a threshold value associated with the first frequency band 710. In some embodiments, the threshold value for a given frequency band may be based on measures of similarity determined for one or more previous sets of audio parameters tested by the audio device 100. In other embodiments, the threshold value for a given frequency band may be selected based on a measure(s) of similarity (e.g., a correlation and/or a coherence) which is likely to indicate that the user accurately perceived the portion of the audio sample associated with that frequency band.

If the measure of similarity associated with the first frequency band 710 is above the threshold value associated with the first frequency band 710, then the calibration application 112 may determine that the audio parameter(s) accurately represents the hearing characteristics of the user, and the method 300 terminates. If the measure of similarity associated with the first frequency band 710 is not above the threshold value associated with the first frequency band 710, then the calibration application 112 determines that the audio parameter(s) do not accurately represent the hearing characteristics of the user. The method 300 then proceeds to step 390.

At step 390, the calibration application 112 adjusts one or more audio parameters based on the measure(s) of similarity. For example, and without limitation, if a measure of similarity associated with a particular frequency band indicates that the user is not accurately perceiving a portion of the audio sample associated with that frequency band, then an equalization parameter associated with the frequency band (e.g., a gain value) may be increased or decreased. Again, in various embodiments, step 370 and step 380 are performed by the calibration application 112 for each of a plurality of frequency bands. Accordingly, in such embodiments, the calibration application 112 performs step 390 (e.g., by increasing and/or decreasing an audio parameter associated with a given frequency band) for each frequency band having a measure of similarity that is not above the threshold value.

The method 300 then returns to step 350, where the calibration application 112 provides an additional audio sample to the user via the speaker(s) 120 based on the updated audio parameter(s). Then, at step 360, the calibration application 112 acquires additional cABR data via the electrodes 130 and, at step 370, compares the additional cABR data to a representation of the additional audio sample to determine one or more additional measures of similarity for the updated audio parameters. Next, at step 380, the calibration application 112 again determines whether the additional measure(s) of similarity associated with each frequency band are above a threshold value associated with the frequency band.

If the additional measure(s) of similarity associated with each frequency band are above the threshold values associated with the frequency bands, then the method 300 terminates. If, on the other hand, the additional measure(s) of similarity associated with each frequency band are not above the threshold values associated with the frequency bands, then the method 300 again returns to steps 390, 350, 360, and 370, such that the sound parameters are dynamically modified as the user listens to audio samples (e.g., a music track).

In other embodiments, the calibration application 112 may perform steps 350, 360, and 370 for each a plurality of different sets of sound parameters in order to determine a set of measures of similarity for each set of sound parameters. Then, the calibration application 112 compares the measures of similarity associated with all of the sets of sound parameters to select the sound parameters that most accurately represent the hearing characteristics of the user. The selected sound parameters are then implemented by audio device 100, and the method 300 terminates.

In various embodiments, audio parameters determined for a variety of different audio samples provided to the user may be stored in a database and correlated based on audio characteristics associated with each audio sample. For example, and without limitation, the calibration application 112 could track the audio characteristics (e.g., frequency content) of music tracks provided to the user via the speakers 120 and determine similarities between the audio characteristics and the sound parameters determined via the method 300 of FIG. 3. Then, when the user listens to a new audio sample (e.g., a new music track), the calibration application 112 could compare the audio characteristics associated with the new audio sample to known audio characteristics stored in the database to determine a closest match. The calibration application 112 could then provide the new audio sample to the user via the speakers 120 based on the sound parameters associated with the closest match.

In sum, the calibration application 112 provides a first audio sample to the ears of the user via speakers and acquires auditory brainstem response (ABR) data via electrodes. The calibration application then determines initial audio parameters based on the acquired ABR data. Next, the calibration application provides a second audio sample to the ears of the user based on the initial audio parameters and acquires complex auditory brainstem response (cABR) data. The calibration application then compares the cABR data to a representation of the second audio sample to determine one or more measures of similarity. The calibration application then updates one or more sound parameters based on the measures of similarity.

At least one advantage of the techniques described herein is that signals indicative of user brain activity can be analyzed to more accurately determine sound parameters for multiple frequency bands. Additionally, sound parameters can be determined while a user is listening to various types of complex audio samples, such as a music track, without requiring the user to listen to a lengthy series of tones. Accordingly, the user does not need to spend a significant amount of time and effort calibrating the audio device.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable processors or gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A non-transitory computer-readable storage medium including instructions that, when executed by a processor, configure the processor to determine one or more equalization parameters, by performing the steps of:
  acquiring complex auditory brainstem response (cABR) data associated with an audio sample;
  comparing the cABR data to at least one representation of the audio sample to determine at least one measure of similarity; and
  determining the one or more equalization parameters based on the at least one measure of similarity.

2. The non-transitory computer-readable storage medium of claim 1, wherein comparing the cABR data to the at least one representation of the audio sample comprises:
  filtering the cABR data based on a plurality of frequency bands; and
  for each frequency band, comparing the cABR data associated with the frequency band to the representation of the audio sample associated with the frequency band to determine at least one measure of similarity.

3. The non-transitory computer-readable storage medium of claim 2, wherein, for each frequency band, the representation of the audio sample comprises at least one of a wavelet and spectrographic data associated with the frequency band.

4. The non-transitory computer-readable storage medium of claim 2, wherein, for each frequency band, comparing the cABR data to the representation of the audio sample comprises comparing a first wavelet associated with the cABR data to a second wavelet associated with the representation of the audio sample.

5. The non-transitory computer-readable storage medium of claim 1, wherein the audio sample comprises at least one of a voice sample and a music sample.

6. The non-transitory computer-readable storage medium of claim 1, wherein determining the one or more equalization parameters based on the at least one measure of similarity comprises modifying one or more gain values, and wherein each of the gain values is associated with a different frequency band.

7. The non-transitory computer-readable storage medium of claim 1, further comprising:
reproducing a second audio sample based on the one or more equalization parameters;
acquiring second cABR data associated with the second audio sample;
comparing the second cABR data to at least one representation of the second audio sample to determine at least one additional measure of similarity; and
modifying at least one of the one or more equalization parameters based on the at least one additional measure of similarity.

8. The non-transitory computer-readable storage medium of claim 7, wherein both the first audio sample and the second audio sample correspond to a music sample, and the one or more equalization parameters are dynamically modified as a user listens to the music sample.

9. The non-transitory computer-readable storage medium of claim 1, further comprising, prior to acquiring the cABR data:
acquiring auditory brainstem response (ABR) data associated with a second audio sample; and
determining one or more initial equalization parameters based on the ABR data, wherein each initial equalization parameter included in the one or more initial equalization parameters is associated with a different frequency band,
wherein the cABR data is acquired by reproducing the audio sample based on the one or more initial equalization parameters.

10. A system for determining one or more equalization parameters, the system comprising:
at least one speaker configured to reproduce an audio sample;
one or more electrodes configured to acquire complex auditory brainstem response (cABR) data associated with the audio sample; and
a processor coupled to the at least one speaker and the one or more electrodes and configured to:
compare the cABR data to one or more wavelets associated with the audio sample to determine at least one measure of similarity; and
determine the one or more equalization parameters based on the at least one measure of similarity.

11. The system of claim 10, wherein the processor is configured to compare the cABR data to the one or more wavelets associated with the audio sample by filtering the cABR data based on a plurality of frequency bands, and, for each frequency band, comparing the cABR data associated with the frequency band to a wavelet associated with the frequency band and included in the one or more wavelets to determine at least one measure of similarity.

12. The system of claim 11, wherein the processor is further configured to generate, for each frequency band, a second wavelet based on the cABR data associated with the frequency band.

13. The system of claim 12, wherein the processor is configured to compare the cABR data associated with each frequency band to the wavelet associated with the frequency band by comparing each second wavelet to a corresponding wavelet included in the one or more wavelets.

14. The system of claim 12, wherein the processor is configured to compare the cABR data associated with each frequency band to the wavelet associated with the frequency band by computing at least one distance between each second wavelet and a corresponding wavelet included in the one or more wavelets.

15. The system of claim 10, wherein the one or more electrodes are coupled to at least one headphone and are configured to acquire the cABR data via a surface of an ear canal of a user.

16. The system of claim 10, wherein the audio sample comprises a music sample, and the one or more equalization parameters are dynamically modified based on the at least one measure of similarity as a user listens to the music sample.

17. The system of claim 10, wherein the processor is further configured to determine one or more initial equalization parameters based on auditory brainstem response (ABR) data associated with a second audio sample, and the cABR data is acquired by reproducing the audio sample based on the one or more initial equalization parameters.

18. The system of claim 10, wherein the processor is further configured to determine a measure of similarity between the audio sample and a music sample, and, based on the measure of similarity, determine that the at least one speaker should reproduce the music sample based on the one or more equalization parameters.

19. A method for determining one or more equalization parameters, the method comprising:
acquiring, via one or more electrodes, auditory brainstem response (ABR) data associated with a first audio sample;
determining, via a processor, one or more equalization parameters based on the ABR data;
reproducing a second audio sample based on the one or more equalization parameters;
acquiring, via the one or more electrodes, complex auditory brainstem response (cABR) data associated with the second audio sample;
comparing, via the processor, the cABR data to at least one representation of the second audio sample to determine at least one measure of similarity; and
modifying the one or more equalization parameters based on the at least one measure of similarity.

20. The method of claim 19, wherein comparing the cABR data to the at least one representation of the second audio sample comprises:
filtering the cABR data based on a plurality of frequency bands; and
for each frequency band, comparing the cABR data associated with the frequency band to the representation of the second audio sample associated with the frequency band to determine at least one measure of similarity.

* * * * *